United States Patent [19]
Lindstrom

[11] Patent Number: 6,090,141
[45] Date of Patent: Jul. 18, 2000

[54] SMALL INTRACORNEAL LENS

[76] Inventor: Richard L. Lindstrom, 2811 Westwood Rd., Wayzata, Minn. 55391

[21] Appl. No.: 08/910,734

[22] Filed: Aug. 13, 1997

Related U.S. Application Data

[63] Continuation-in-part of application No. 08/484,072, Jun. 7, 1995, abandoned, which is a continuation of application No. 08/026,597, Mar. 5, 1993, abandoned.

[51] Int. Cl.[7] .................................................. A61F 2/14
[52] U.S. Cl. ................................................. 623/5; 623/4
[58] Field of Search .............................. 623/4–6; 351/161

[56] References Cited

U.S. PATENT DOCUMENTS

| | | | |
|---|---|---|---|
| Re. 25,286 | 11/1962 | De Carle | 351/161 |
| 3,415,597 | 12/1968 | Harman | 351/161 |
| 4,715,858 | 12/1987 | Lindstrom | 623/5 |
| 4,798,608 | 1/1989 | Grendahl | 623/6 |
| 4,851,003 | 7/1989 | Lindstrom | 623/5 |
| 4,890,912 | 1/1990 | Visser | 351/161 |
| 4,971,432 | 11/1990 | Koeniger | 351/161 |
| 4,994,080 | 2/1991 | Shepard | 623/5 |
| 5,089,024 | 2/1992 | Christie et al. | 623/6 |
| 5,158,572 | 10/1992 | Nielsen | 623/6 |
| 5,196,026 | 3/1993 | Barrett et al. | 623/5 |
| 5,336,261 | 8/1994 | Barrett et al. | 623/5 |

*Primary Examiner*—Michael J. Milano
*Assistant Examiner*—Dinh X. Nguyen
*Attorney, Agent, or Firm*—Hugh D. Jaeger

[57] ABSTRACT

An intracorneal lens that is inserted between stromal layer of a cornea of an eye, and provides two distinct regions of focality. The lens includes a central region with a thinner wall and a surrounding region with a thicker wall.

6 Claims, 5 Drawing Sheets

SMALL INTRACORNEAL LENS

CROSS REFERENCES TO CO-PENDING APPLICATIONS

This patent application is a continuation-in-part of Ser. No. 08/484,072 entitled "Small Intracorneal Lens" filed on Jun. 7, 1995, which is a continuation of Ser. No. 08/026,597, entitled "Small Intracorneal Lens" filed on Mar. 5, 1993, by the same inventor, both now abandoned.

BACKGROUND OF THE INVENTION

1. Field of the Invention

The present invention is for an intracorneal lens, and more particularly, pertains to a small intracorneal lens with two regions of focality.

2. Description of the Prior Art

Three prior art patents, Choyce (U.S. Pat. No. 4,607,617), Grendahl (U.S. Pat. No. 4,624,669) and Lindstrom (U.S. Pat. No. 4,851,003), for intracorneal lenses describe large lenses or do not teach a bifocal or multifocal effect.

Barrett et al. (U.S. Pat. No. 5,196,026) describe a small intracorneal lens that does not significantly impede nutrient flow through the cornea and only involves a small optical region of the cornea. The region of cornea that surrounds the perimeter of the device of Barrett et al. is not optically affected by their lens. Barrett disclose a "bull's-eye" intracorneal lens that contains a hole drilled out of the center of the lens which will allow flow of nutrients through the cornea. One does not know from the Barrett et al. description if the aperture made in the lens should be a pin hole or if it should be large in comparison to the optical zone of the cornea. Barrett et al. teach a smaller lens that does not require an aperture and does not impede nutrient flow due to its small diameter size.

Shepard (U.S. Pat. No. 4,994,080) discloses a lens that has an aperture in it, but it is not suitable for an intracorneal inlay. Shepard describes an optical lens that has application for a contact lens, a corneal overlay, or as an artificial implanted lens replacement. The lens has at least one, but can contain several, small pin holes, which are referred to as stenopaeic openings. These openings are intended to pass only those light beams that are parallel to the central axis of the stenopaeic opening back onto the retinal portion of the eye. This method of light focusing through pin holes can be very limiting in terms of field of view and limits the size of image that can be adequately focused. It is furthermore doubtful that such a lens would have any application as an intracorneal inlay due to the anticipated growth of corneal stromal tissue into the pin hole of Shepard's device, thereby limiting its usefulness as an intracorneal lens.

The present intracorneal inlay device is designed to overcome the limitations of prior art devices and provide for multifocality.

The present invention overcomes the disadvantages of the prior art by providing a small intracorneal lens where the intracorneal lens provides two focal regions of specific configuration. The central region provides adequate area for imaging at one focal length, and the surrounding area provides imaging at a second focal length. The transition is designed to minimize distortion of the image.

SUMMARY OF THE INVENTION

The invention comprises an intracorneal lens that is inserted between stromal layers of the cornea and provides two distinct regions of focality. The primary embodiment discloses two distinct regions of the disc-shaped lens comprising a central region with a specific thinner wall thickness configuration and its associated focality and a surrounding region with a thicker wall thickness configuration and a second focality. The central region can be constructed such that it provides some optical correction to the central region or it can be made so that it provides no additional correction or change to the normal focal length provided by the cornea. The surface configuration for either the central or surrounding region on either the anterior or posterior side of the lens can be concave, convex or planar. The transition from the thinner central region to the thicker surrounding region can be made gradual to avoid edge effects that may distort the image. The transition can also consist of a sharp step change in thickness or it can be rounded. The entire lens can be constructed of a permeable material, such that oxygen and other nutrients can flow through the cornea at the lens implant site. The central region can be constructed from a material of different refractive index from that of the surrounding region. The central region can be configured such that the thickness is completely reduced to zero providing an open central region with a focality provided entirely by the natural cornea.

Having thus described embodiments of the present invention, it is the principal object of the present invention to provide an intracorneal lens which provides two regions of focality.

One object of the present invention is to provide a small intracorneal lens where the cornea, along with the central region of the lens, provides one focal plane, and the surrounding region of the intracorneal lens and the cornea provides a second focal plane. The central region is contiguous with the surrounding region forming a transition region between them that does not distort the image due to edge effects. The central region can have a thinner lens configuration than the surrounding region, and the surfaces of either the central region or the surrounding region can be either convex, concave or planar. The diameter of the central region can range from 1.0 to 2.5 mm, with a preferable diameter of 1.5 to 2.0 mm. The diameter of the surrounding region can range from 2.5 to 4.5 mm, with a preferable diameter of 3.0 to 4.0 mm. A similar bifocal or multifocal effect can also occur with the use of a single lens structure with one focality occurring through the lens and another focality occurring around the lens and through the cornea alone. This is not the intent of the present invention which provides bifocality from the central and surrounding regions of the present lens in combination with the cornea. The present lens can be used to form three regions of focality wherein two focal regions are provided by the central and surrounding regions of the present lens in combination with the cornea, and a third region of focality is formed in the region of the cornea surrounding the lens. The three regions of focality could be used to provide near, middle and far range of vision, for example.

Another object of the present invention is a small intracorneal lens in which the cornea alone provides for one focal plane in the central region, and the surrounding region of the lens with the cornea provides a second focal plane. Here the thickness of the lens in the central region has been reduced to zero and eliminated. Consideration of edge effects at the transition between central and surrounding regions and the diameters of the central region and the surrounding region are the same as described in the first object of the present invention.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

An intracorneal lens with bifocality is needed to provide those patients with myopia, presbyopia, hyperopia or other visual ailments of the eye an opportunity to image objects both near and far using different regions of the intracorneal lens in combination with their natural cornea. In the current invention, the central region of the lens is configured with an optical surface with a specific wall thickness configuration. Generally, the wall thickness configuration of the central region is thinner than the wall thickness configuration of the surrounding region of the lens, although this is not a requirement. The central region wall thickness configuration can also be such that lens material is completely absent from the central region of the intracorneal lens. The central region is contiguously joined to the surrounding region by a transition region. The thickness configuration of the transition region provides minimal distortion to the image due to edge effects that can occur at the edge of or within the transition region.

The patient with such a bifocal intracorneal lens can view an object at one focal length using the focality provided by the central region of the lens plus the cornea and can view an object at a second focal length using the focality provided by the surrounding region of the lens plus the cornea. Either the central region or the surrounding region can provide a greater or lesser focal length than the other region. This is achieved by altering the surface geometry of the intracorneal lens in the central region and the surrounding region independently. Considering that the normal cornea has a convex/concave outer and inner surface geometry, respectively, the intracorneal lens can have a surface geometry for either the central region or the surrounding region and for either the anterior or posterior surface that is either convex, concave or forms a planar surface. The amount of concavity and convexity can also be modified within the geometrical constraints of the human eye anatomy and can have more or less geometrical convexity or concavity than that found in the normal cornea.

The intracorneal lens can also provide for yet a third region for focality around the outside of the surrounding region.

The small intracorneal lens 30 is to treat low hyperopia and myopia. The powers of the lens can range from −0.50 diopters to −10 diopters and +0.50 diopters to +10 diopters. One purpose is for low corrections, particularly −0.50 to −5 diopters to +0.50 to +5 diopters. Especially, the small intracorneal lens can be used for the correction of presbyopia. The lens has two regions of different focal length, thereby providing two different corrections, one for the central region and another for the surrounding region.

Figure 1:
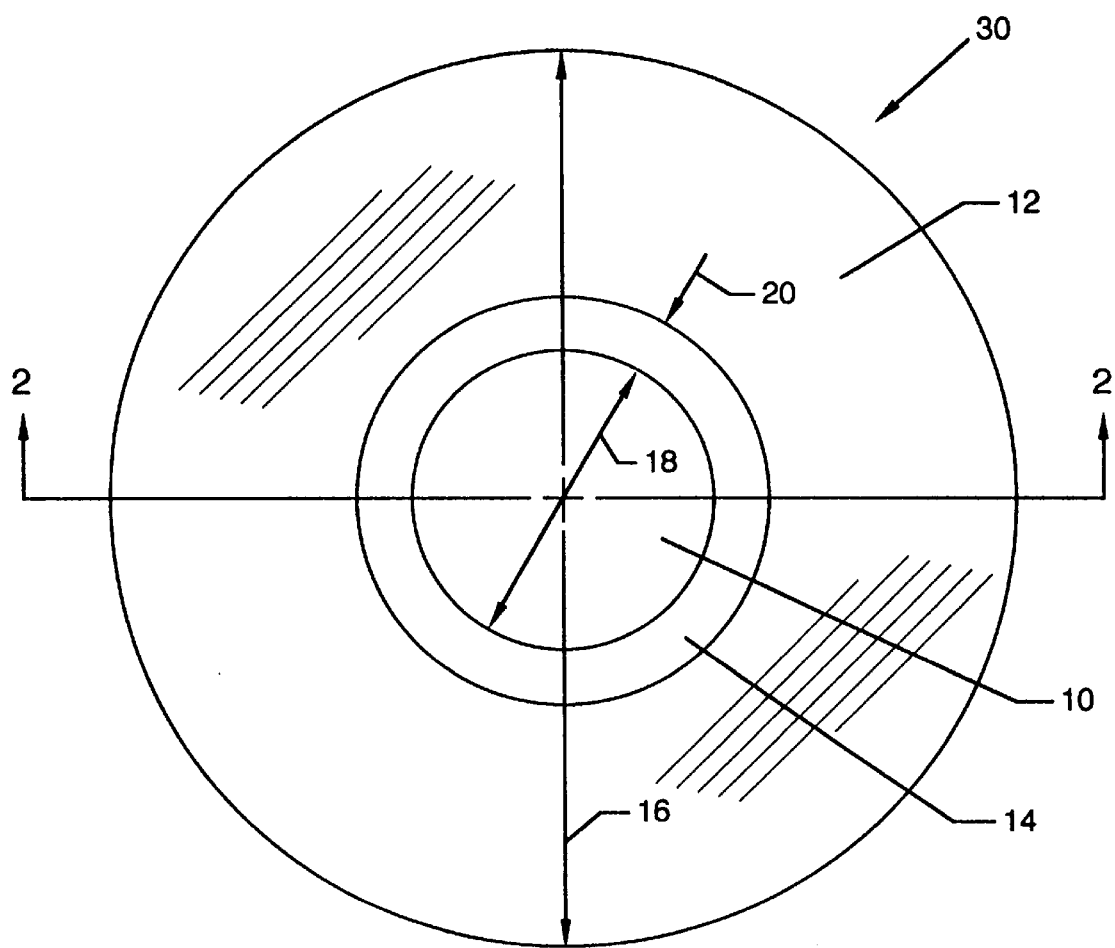
FIG. 1 illustrates a plan view of a small intracorneal lens.
Figure 2:
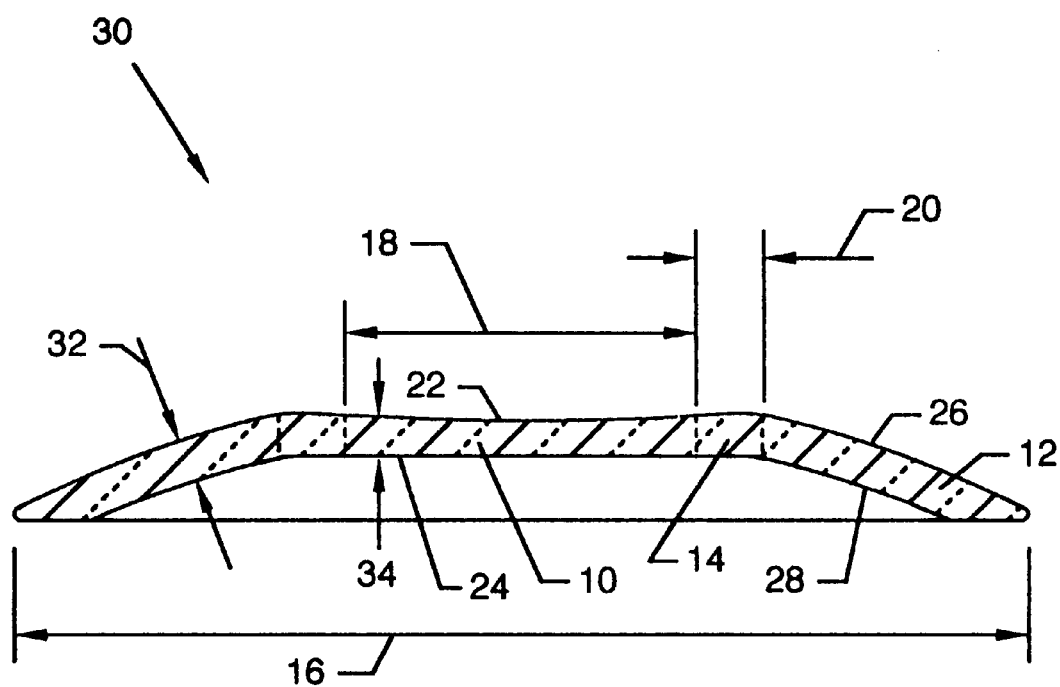
FIG. 2 illustrates a cross-sectional view of the small intracorneal lens taken along line 2—2 of FIG. 1.

FIGS. 1 and 2 illustrate a small intracorneal lens 30 with a central region 10 having a central diameter 18 that can range from 1.0 to 2.5 mm but preferably is from 1.5 to 2.0 mm. This diameter is large enough to allow adequate passage of light to form a usable image on the retina. The surrounding region 12 has an outer diameter 16 that ranges from 2.5 to 4.5 mm but preferably ranges from 3.0 to 4.0 mm. The transition region 14 is contiguous with the central region and the surrounding region and has a transition width 20 that ranges from zero to 1.0 mm but preferably ranges from 0.1 to 0.5 mm. The central region 10 has an outer surface 22 and an inner surface 24 either of which can be concave, convex or planar. In FIG. 2, the outer surface 22 is shown to be concave and the inner surface 24 is shown to be planar. The surrounding region 12 of the lens has an outer surface 26 and an inner surface 28 either of which can be concave, convex or planar. As shown in FIG. 2, the outer surface 26 is convex and the inner surface 28 is concave. The amount of convexity and concavity for the inner surface or outer surface can differ from each other and can vary depending upon the optical needs of the patient. This lens, for example, could be used to treat a patient with hyperopia wherein the central region makes only slight correction for distant vision and the surrounding region corrects optically for close vision. Alternately, the lens can be used to correct for myopia vision with bifocality occurring between the central region and the surrounding region. The lens can allow corrections of up to positive 10 diopters or negative 10 diopters depending upon the configurations of the lens surfaces and the thickness of the lens. The thickness 32 of the surrounding region 12 can range from 0.1 to 1 mm, with a preferred thickness of 0.3 to 0.6 mm. The thickness 34 of the central region 10 can range from zero to 1 mm, with a preferred thickness of 0.2 to 0.5 mm. The small intracorneal lens can be constructed from a suitable material such as PMMA, polycarbonate, polysulfone, hydrogel, silicone or other polymer material. The outer edge of the surrounding region is rounded and smooth.

Figure 3:
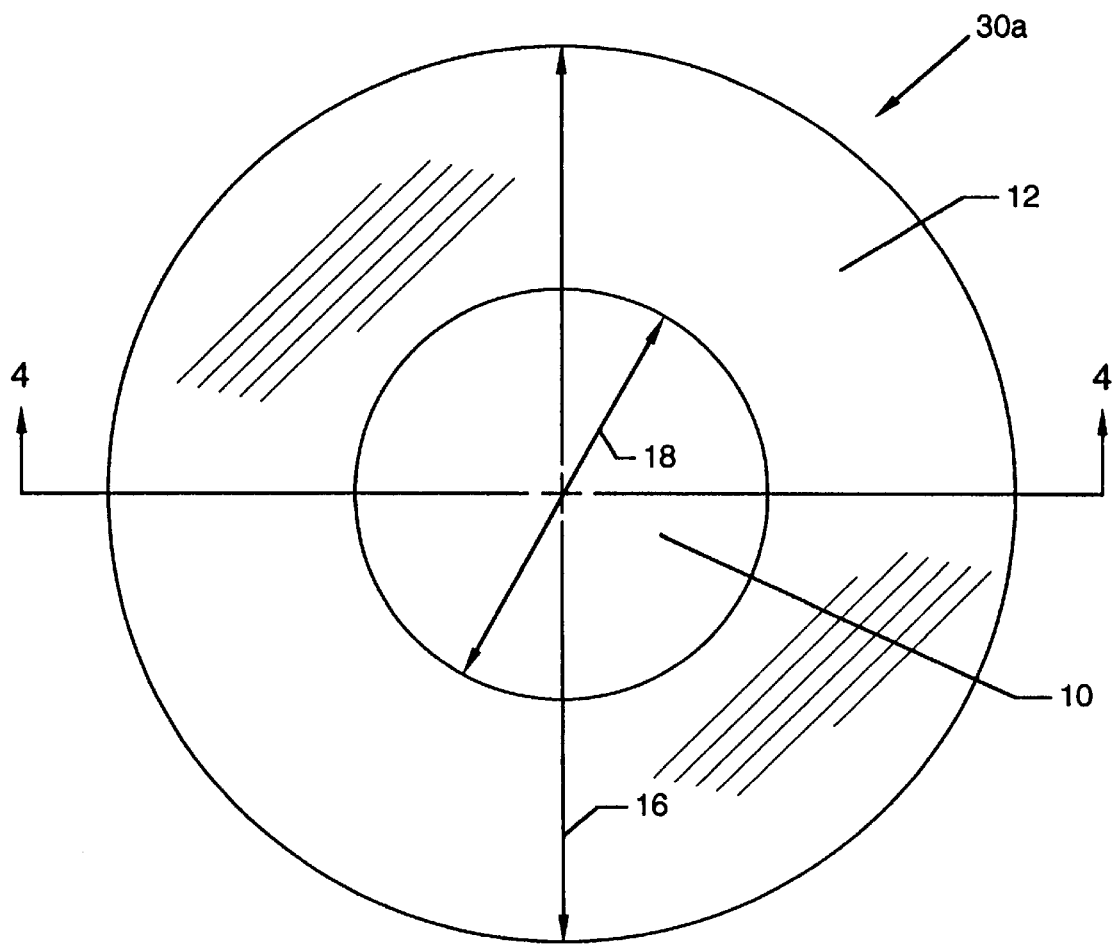
FIG. 3 illustrates a plan view of a first alternative embodiment of a small intracorneal lens.
Figure 4:
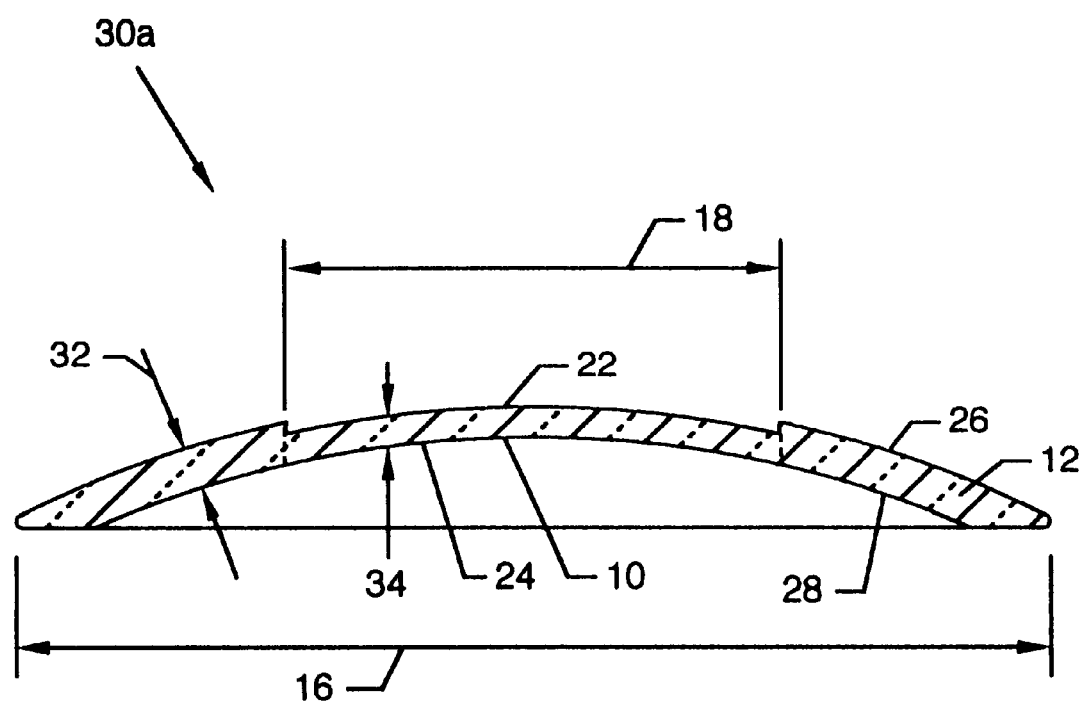
FIG. 4 illustrates a cross-sectional view of the first alternative embodiment taken along line 4—4 of FIG. 3; and, FIG. 5 illustrates a cross-sectional view of a second alternative embodiment of a small intracorneal lens.

FIGS. 3 and 4 illustrate a first alternative embodiment of the intracorneal lens, labeled 30a, with all other numbers indicative of the same lens components and dimensions as found in FIGS. 1 and 2. Here the transition region 14 has been omitted and an abrupt transition is shown without gradual tapering from the central region 10 to the surrounding region 12, although tapering could occur between regions. Here the central region 10 is shown with a convex outer surface 22 and a concave inner surface 24. The surface configuration for the inner or outer surface can be convex, concave or planar. The central region 10 can be constructed of a material of the same refraction properties as that of the surrounding region 12 or it can be made form a material of different refractive index. The central region 10 can also be omitted, thereby providing an open aperture and refractive index representative of the cornea alone, as illustrated in FIG. 5, next described.

Figure 5:
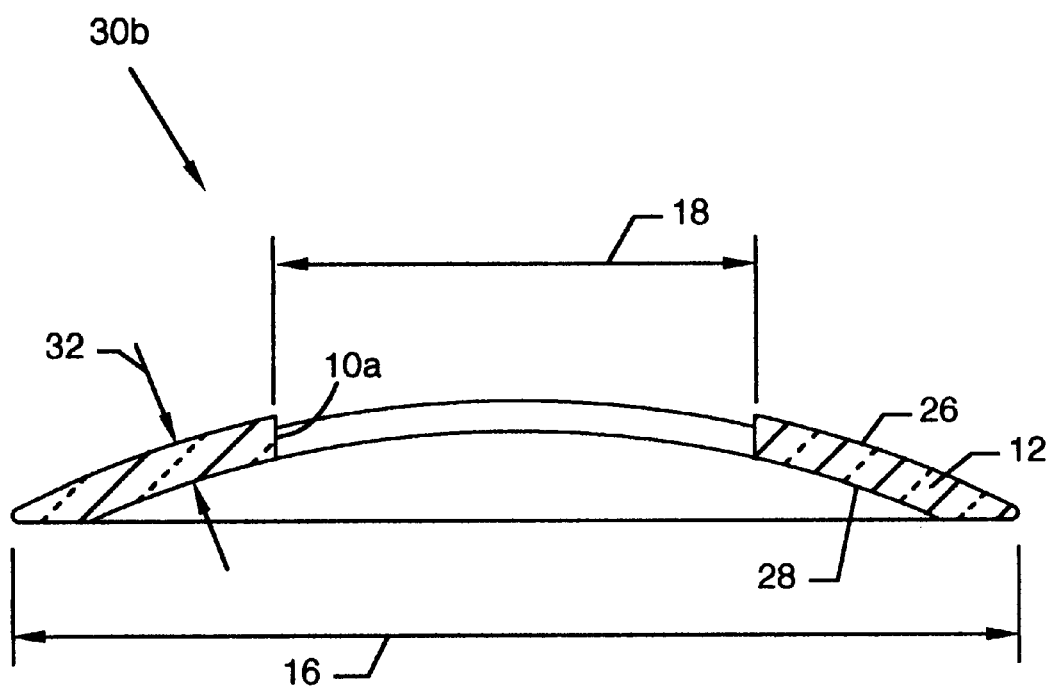

FIG. 5 illustrates a second alternative embodiment of the intracorneal lens, labeled 30b, with the central region 10 omitted, thereby providing an open circular aperture 10a for providing an optical focality derived solely from the cornea alone. All other numerals in FIG. 5 are indicative of the same lens components and dimensions as found in the other drawing figures and as previously described.

Various modifications can be made to the present invention without departing from the apparent scope hereof.

I claim:

1. An intracorneal lens for implant within the stromal tissue of the cornea, comprising:

a. a circular central region constructed to provide a first optical focality in combination with the cornea;

b. a circular surrounding region concentric with said circular central region and constructed to provide a second optical focality in combination with the cornea;

c. said circular surrounding region being joined with said circular central region at a circular transition region;

d. said circular central region having a diameter of 1.0 to 2.5 mm, an outer surface, an inner surface, and a thickness between said outer surface and said inner surface, said outer surface and said inner surface each having a configuration selected from the group of configurations consisting of concave, convex and planar;

e. said circular surrounding region having an outside diameter which is greater than the diameter of said circular central region but not more than 4.5 mm, a convex outer surface, a concave inner surface, a peripheral edge, a constant thickness portion between said convex outer surface and said concave inner surface which extends from said circular transition region to a location closely adjacent to said peripheral edge, and a tapering thickness portion between said convex outer surface and said concave inner surface which extends from said location closely adjacent to said peripheral edge to said peripheral edge;

f. said thickness of said circular central region being thinner than said constant thickness portion of said circular surrounding region; and, g. said intracorneal lens being shaped, sized and configured to be implanted within the stromal tissue of the cornea.

2. The intracorneal lens of claim 1, wherein said circular transition region is constituted by an abrupt change in thickness from said circular central region to said circular surrounding region.

3. The intracorneal lens of claim 1, wherein said circular transition region has a width and has outer and inner surfaces which merge smoothly with the respective outer and inner surfaces of said circular central region and said circular surrounding region.

4. The intracorneal lens of claim 1, wherein the thickness of said constant thickness portion of said circular surrounding region is 0.1 to 1.0 mm.

5. An intracorneal lens for implant within the stromal tissue of the cornea, comprising:

a. a circular central region defined by a circular aperture for providing a first optical focality derived solely from the cornea;

b. a circular surrounding region concentric with said circular aperture and constructed for providing a second optical focality in combination with the cornea;

c. said circular aperture having a diameter of 1.0 to 2.5 mm;

d. said circular surrounding region having an outside diameter which is greater than the diameter of said circular aperture but not more than 4.5 mm, a convex outer surface, a concave inner surface, a peripheral edge, a constant thickness portion between said convex outer surface and said concave inner surface which extends from said circular aperture to a location closely adjacent to said peripheral edge, and a tapering thickness portion between said convex outer surface and said concave inner surface which extends from said location closely adjacent to said peripheral edge to said peripheral edge; and, e. said intracorneal lens being shaped, sized and configured to be implanted within the stromal tissue of the cornea.

6. The intracorneal lens of claim 5, wherein the thickness of said constant thickness portion of said circular surrounding region is 0.1 to 1.0 mm.

\* \* \* \* \*